United States Patent [19]

Giovanniello et al.

[11] Patent Number: 4,871,525

[45] Date of Patent: Oct. 3, 1989

[54] ANTIPERSPIRANT COMPOSITION AND METHOD OF PREPARATION

[75] Inventors: Rocco Giovanniello, Port Jervis; Stephen M. Howe, Walden, both of N.Y.

[73] Assignee: Westwood Chemical Corporation, Middletown, N.Y.

[21] Appl. No.: 81,638

[22] Filed: Aug. 3, 1987

Related U.S. Application Data

[63] Continuation-in-part of Ser. No. 922,753, Oct. 24, 1986, abandoned, which is a continuation of Ser. No. 817,047, Jan. 8, 1986, abandoned.

[51] Int. Cl.$^4$ .................... C01F 7/56; C01G 25/04; A61K 7/34
[52] U.S. Cl. .................... 423/463; 423/462; 424/66
[58] Field of Search .................... 423/462, 463; 424/66

[56] References Cited

U.S. PATENT DOCUMENTS

| | | | |
|---|---|---|---|
| 2,814,584 | 11/1957 | Daley | 424/66 |
| 2,854,382 | 9/1958 | Grad | 424/66 |
| 2,906,668 | 9/1959 | Beckman | 423/463 |
| 3,476,509 | 11/1969 | Jones | 423/462 |
| 3,792,068 | 2/1974 | Luedders | 424/66 |
| 3,903,258 | 9/1975 | Siegal | 424/66 |
| 3,947,556 | 3/1976 | Jones et al. | 423/463 |
| 3,998,788 | 12/1976 | Rubino | 424/66 |
| 4,331,609 | 5/1982 | Orr | 424/66 |
| 4,359,456 | 11/1982 | Gosling et al. | 423/462 |
| 4,435,382 | 3/1984 | Shin et al. | 424/66 |
| 4,605,554 | 8/1986 | Prussin et al. | 424/66 |
| 4,775,528 | 10/1988 | Callaghan et al. | 424/260 |

FOREIGN PATENT DOCUMENTS

| | | | |
|---|---|---|---|
| 61863 | 5/1975 | Australia | 423/463 |
| 1353916 | 5/1974 | United Kingdom . | |
| 142993 | 3/1976 | United Kingdom | 423/463 |
| 2144992 | 3/1985 | United Kingdom | 423/463 |

*Primary Examiner*—John Doll
*Assistant Examiner*—Jeffery E. Russel
*Attorney, Agent, or Firm*—Anthony Lagan, Jr.

[57] ABSTRACT

Aluminum zirconium hydroxy halide glycinate complex and a method of its preparation is disclosed having an empirical formula:

$$Al_2(OH)_{6-y}X_y ZrO(OH)_x Cl_{2-x}/\text{Neutral Amino Acid}$$

wherein x has a numerical value of 0 to 1.5, y has a numerical value of 0.7 to 3.0, X is chlorine, bromine or iodine, and whose polymer distribution as characterized by a size exclusion chromatograph is:

(a) a peak height ratio of peak 4 to peak 3 of 0.5 to 1.8:1, and
(b) peaks (1+2) contain less than 4% of the polymer distribution by weight.

24 Claims, 3 Drawing Sheets

RATIO HEIGHT PEAK 4/HEIGHT PEAK 3:1.0:1
PERCENT POLYMERS IN PEAKS (1+2):0.43%

RATIO HEIGHT PEAK 4/HEIGHT PEAK 3:0.2:1
PERCENT POLYMERS IN PEAKS (1+2):27.19%

RATIO HEIGHT PEAK 4/HEIGHT PEAK 3:<0.2:1
PERCENT POLYMERS IN PEAKS (1+2):16.71%

RATIO HEIGHT PEAK 4/HEIGHT PEAK 3:1.0:1
PERCENT POLYMERS IN PEAKS (1+2):0.57%

RATIO HEIGHT PEAK 4/HEIGHT PEAK 3:1.0:1
PERCENT POLYMERS IN PEAKS (1+2):0.43%

RATIO HEIGHT PEAK 4/HEIGHT PEAK 3: 2.9:1
PERCENT POLYMERS IN PEAKS (1+2): 16.03%

4 HOURS AT 95°C

RATIO HEIGHT PEAK 4/HEIGHT PEAK 3: 3.9:1
PERCENT POLYMERS IN PEAKS (1+2): 10.98%

1 HOUR AT 95°C

ANTIPERSPIRANT COMPOSITION AND METHOD OF PREPARATION

FIELD OF THE INVENTION

This invention relates to a composition and method of preparing a composition having improved antiperspirant activity. In particular, an Aluminum Zirconium Hydroxyl Halide Glycinate complex which is polymerically distinct from conventional Aluminum Zirconium salt complexes is disclosed.

This application is a continuation in part of a continuation application entitled "BASIC ALUMINUM HALIDES", Ser. No. 922,753, with a filing date of Oct. 24, 1986, now abandoned, which in turn is a continuation of a U.S. application of the same title, Ser. No. 817,047, filed Jan. 8, 1986, now abandoned.

BACKGROUND OF THE INVENTION

Basic aluminum halides (also referred to as aluminum halohydrates) have long been known to possess antiperspirant activity. These antiperspirant compositions are available in the form of polymeric compositions having the empirical formula:

$$Al_2(OH)_{6-y}X_y$$

wherein X is chlorine, bromine or iodine and y has a numerical value from about 0.7 to about 3.

However, it is only in recent studies, as described in U.S. Pat. No. 4,359,456 (the '456 patent), that it has been shown by size exclusion chromatography that basic aluminum halides are composed of individual polymer bonds which pertain to different molecular weight groups of the compound. In these studies of basic aluminum halides obtained by conventional methods of preparation it was shown that it can further be broken down from high molecular weight polymers by diluting concentrated aqueous solutions thereof to lower aqueous concentrations with heat and/or aging at room temperature to produce more effective antiperspirants as shown in sweat reduction panel studies.

The '456 patent describes processes for the preparation of improved antiperspirant compositions of aluminum halohydrates, which involve heating a 2.5 to 8.5% aluminum by weight aqueous solution of an aluminum halohydrate of the formula:

$$Al_2(OH)_{6-y}X_y nH_2O$$

where x is chlorine, bromine or iodine and y has a numerical value from about 0.7 to about 3 and n has a numerical value from about 0.8 to about 4, at a temperature of 50° to 140° C. for a period of time to impart to the aluminum product certain desired properties in respect of size exclusion chromatography test bands. The products thus obtained from these processes have good antiperspirant activity, but the processes do not provide compositions containing larger amounts of the lower molecular weight polymers with a narrow polydispersity which are believed to possess greater antiperspirant activity.

Zirconyl hydroxyl chloride and alumina chlorhydroxide containing compositions are also known to have antiperspirant activity as disclosed in Great Britain Patent No. 2,144,992, published Mar. 20, 1985, entitled "ANTIPERSPIRANTS" (the British Patent). The product is prepared by heating a 2 to 20% aqueous solution to the compounds to at least 50° C. until a ratio of the heights of peak 4 to peak 3 as measured by gel permeation chromatography exceeds 2:1. The resulting product contains lower molecular weight polymers to increase efficacy, but is also has a wider polydispersity, a higher form of aluminum to zirconium glycinate complex and a lower cationic charge when compared to the novel composition. This is evident from higher molecular weight polymers found in peaks (1+2) as shown in the U.K. Patent No. 2,144,992. Moreover, the novel composition has been tested and shown to be more effective in reducing perspiration than the known product in clinical sweat reduction panel studies, where a substantial amount of reduction was observed with the novel product.

SUMMARY OF THE INVENTION

The novel composition is prepared by mixing an 8-35% aqueous solution at 50° to 100° C. of Component A made up of basic aluminum halide complexes and a neutral amino acid, such as glycine, with 20-50% aqueous solution of Component B made of a zirconyl hydroxychloride solution, and a neutral amino acid such as glycine. The temperature of the mixture of Components A and B is maintained at 50°-100° C. for less than two hours and then immediately dried and chromatographically analyzed to determine a product having a height ratio of peak 4 to peak 3 of 0.5 to 1.8:1, with peaks (1+2) making up less than 4% of the total weight of the polymers.

DETAILED DESCRIPTION OF A PREFERRED EMBODIMENT

It is an object of this invention to provide compositions containing larger amounts of the more active lower molecular weight polymeric aluminum zirconium hydrohalides.

It is another object of this invention to provide larger amounts of lower molecular weight polymers with the percent of the high molecular weight polymers minimized in the distribution.

It is another object of this invention to provide a process for the preparation of said compositions.

It is a further object of this invention to provide a process for the preparation of these compositions that does not first require the synthesis of the undesirable higher molecular weight polymers and then their degradation to a desired molecular weight range.

It is still another object of this invention to provide a process for the preparation of said composition from lower polymeric forms.

Other objects will appear from the description which follows.

The inventive composition is composed of Component A of an aqueous solution of polymeric basic aluminum halides and Component B of zirconyl hydroxychloride solution. Either or both solutions may contain a neutral amino acid to aid in buffering and to prevent gelation in the final composition. The two components are contacted for less than two hours at 50° C. to 100° C. and immediately dried to a powder which when subject to gel permeation chromatography as described in the invention, contains a peak height ratio of peak 4 to peak 3 of 0.5 to 1.8:1, and peaks (1+2) totaling less than 4% of the polymer composition. More particularly, the peak height ratio of peak 4 to peak 3 can be from 0.5 to 1.41:1, e.g., from 0.5 to 1.00:1.

COMPONENT A

In accordance with this invention there is provided a process for the preparation of Component A made of polymeric basic aluminum halides having the empirical formula $$Al_2(OH)_{6-y} X_y n\ H_2O$$

wherein y has a numerical value from about 0.7 to about 3, X is chlorine, bromine or iodine, and n has a numerical value from about 0.8 to about 4, and the polymer distribution as characterized by size exclusion chromatography test is: (a) 100% of the aluminum containing polymers are found in bands II, III and IV, and (b) band III contains at least 20% of the polymers, which comprises heating in water at a temperature from about 50° C. to about 100° C. aluminum metal, preferably in the form of pellets or powder, with a halogen containing compound selected from HX or $AlX_3$ where X is defined above.

The amount of water used is such as to have the concentration of the polymer in percent by weight in the range from about 8 to about 35%, preferably from about 15 to about 25%, and more preferably from about 17 to about 22% by weight.

The reaction temperatures are preferably in the range from about 95 to about 100° C. and should not be high enough to create reflux conditions. Refluxing occurs when a solution is vaporized, then condensed in a common container. It is believed that refluxing the Component A solution will produce the undesired high molecular weight molecules and wider polydispersity reducing antiperspirant activity.

The polymer distribution achieved by the process of invention is one of extremely narrow polydispersity, particularly when the final batch concentration falls within the range of 17–22% and the metal to chloride atomic ratios do not exceed 2.00:1. Such products derived from the invention process can be converted to more stable polymer forms by immediately spray-drying hot aqueous salts to a dry powder as done in conventional spray drying methods.

It is further noted that high temperatures in a range of about 100° C. to 150° C. are not required in the inventive process because the initial combination of the aluminum metal with the halogen containing compound produces an exothermal reaction which only requires the introduction of heat when heat losses are encountered. Further, the rate of the reaction is not critical eliminating the need for a catalyst.

A neutral amino acid, such as glycine, may be present in the solution of Component A to aid in the prevention of gel formation when combined with Component B.

The size exclusion chromatography test was used to determine polymer distributions, contents and relative retention times of band I, II, III and IV on the samples of the compositions of this invention and samples of known compositions. This test is an analytic technique related to high performance liquid chromatogaphy (HPLC). In carrying out the tests a Waters Associates Model 510 pump, a U6K injector, a 401 refractive index detector, and a 730 data module were used for the HPLC instrumentation. One micro Porasil 100 Angstrom GPC column 3.8×30 cm (Waters Cat. No. 27477) were used in the separation.

The directions for carrying out the test are as follows:

In preparing the mobile phase, pipet 2 ml. conc. nitric acid in a 1 liter volumetric flask containing distilled water, dilute to mark and mix. New columns should be conditioned with this mobile phase at least three hours prior to sample testing. Turn pump on to 1.0 ml. per min., flush the reference side of the refractive index cell several minutes and switch to sample side. Referring to the operator manual, zero in the R.I. detector and set the attenuation to 16X. Also set the 730 data module to the following parameter values:

| Parameter No. | Description | Value |
|---|---|---|
| 2 | Chart Speed | 0.6 (cm./min.) |
| 3 | Plot Mode | 0 (Off) |
| 4 | Pen 2 | 0 (Off) |
| 5 | Pen 1 | 10 |
| 7 | Auto Zero | 0 (Off) |
| 8 | L.C. Mode | 1 (Yes) |
| 9 | Calibration | 0 (Analysis) |
| 20 | Auto Parameters | 0 (Off) |
| 21 | Peak Width | 7 |
| 22 | Noise Rejection | 2,000 |
| 23 | Area Rejection | 1,000 |
| 24 | Run/Stop | 6.5 (Min.) |
| 33 | Report % Results | 1 (Yes) |
| 46 | Flow Rate | 1.0 (ml./min.) |
| 47 | Pressure | Column Pressure |
| 48 | Detector/Attenuation | 401/016 |
| 63 | Report Percent Only | 1001 |

The analytical procedure is as follows:

Pipet 0.2 ml. 12 M hydrochloric acid into a 25 ml. volumetric flask containing distilled water, dilute to mark and mix.

After the detector and columns have reached equilibrium as seen by the stability of the response on parameter 51, set parameter 51 to read 5,000–10,000 by turning the optical zero knob on the detector, being certain that operating temperatures within the room remain constant since the slightest change in the temperature will be sensed by the R.I. detector which will create a baseline drift.

Inject a 15 $\mu$l sample of 0.1N hydrochloric acid standard and observe its retention time (the retention time in this analytic test was found to be 5.70 minutes). Set parameters 81 and 82 to retention time values of 5.40 and 6.00 minutes which will inhibit and resume integration without integrating the hydrochloric acid band itself which contains no aluminum polymers.

Dilute all basic aluminum halides to approximately a 10% active level with distilled water, filter the sample through a 0.45 $\mu$ filter and inject a 3.0 $\mu$l sample for the test. The chromatography will show which aluminum containing polymer bands are present, the retention times of each band and their calculated percents.

CALCULATION

% Band to be determined =

$$\frac{\text{(area percent of band to be determined)}}{\text{Total area percent of Al containing bands}}$$

It is known that during stages of basic aluminum halide synthesis via conventional methods of preparation, higher molecular weight polymers, pertaining to aluminum polymers of the band I range, are developed and their percent composition against the total polymer content increases with increasing metal to chloride atomic ratio. Table I shows the percent of Band I polymers found at various reaction states of aluminum chlorhydrate preparation when prepared by the conventional method.

TABLE 1

| Aluminum/Chloride Atomic Ratio | % Band I Aluminum Polymers |
|---|---|
| 1.32:1 | 15.9 |
| 1.82:1 | 17.0 |
| 1.93:1 | 37.2 |

In addition to the formation of Band I, it is also known that basic aluminum halides produced via conventional methods of synthesis contain lower amounts of Band III than those amounts found using the process of this invention.

COMPONENT B

Further, in accordance with the invention, there is provided a process for preparing zirconyl hydroxychloride of the empirical formula:

ZrO $(OH)_xCl_{2-x}$ wherein x has a numerical value of 0–1.5.

Preferably, a 50% zirconyl hydroxychloride solution with a metal to chloride atomic ratio of 0.6–1.2:1 is prepared.

The amount of water used is such as to have a concentration of the component in percentage by weight in the range from 20–55%, but more preferably 50–55%. By using the higher concentration range, the rate of complexing between the amino acid and the basic zirconium halide is greatly retarded and thus allows for a lower form of complex in the final product. The solution is heated to a temperature of 50° C. and a neural amino acid, such as glycine, may be added to the solution to form a zirconyl chloride-glycinate complex. The atomic ratio of glycine to zirconium is in the range of 0–3.0:1, and more preferably is 0.5:1.

ALUMINUM-ZIRCONIUM HYDROXY HALIDE GLYCINATE COMPLEX

Once component A and Component B are mixed, an aluminum-zirconium hydroxy halide glycinate complex of the empirical formula:

$Al_2(OH)_{6-y}X_y/ZrO(OH)_xCl_{2-x}$/neutral amino acid x=0.0–1.5, X=Cl, Br, I, y=0.7–3.0 wherein x, y and X are as defined above, is prepared. The aluminum zirconium atomic ratio and the metal/-neutral amino acid atomic ratio should preferably be 2.0–8.0 and 1.0–10.0:1, respectively.

Preferably an 8–35% solution of Component A at a temperature of 50°–100° C. is mixed with a 20–55% solution of Component B resulting in a combined solution temperature of 50°–100° C. Either or both components may contain a neutral amino acid prior to mixing.

More preferably, a 20% solution of Component A at 97° C. is mixed with a 50% solution of Component B at 50° C. to form a combined solution at 85° C.

Contact time of Component A and B should not exceed two hours to minimize the formation of higher polymer forms found in peaks (1+2) when analyzed by gel permeation chromatography. The contact time is less than two hours, but preferably less than 30 minutes.

The combined solution should be immediately dried to a powder and when analyzed by gel chromatography it should contain a peak 4 to peak 3 height ratio of 0.5–1.8:1. Peaks (1+2) should contain less than 4% of the total polymer composition by weight. The shorter the contact time of the combined solution, the lower is the amount of undesirable high molecular weight zirconium polymers formed in peaks (1+2), the lower is the degree of glycinate complex, the higher is the cationic charge of the molecule and as a result, a more efficacious salt is obtained.

The examples showing the processes and compositions of this invention are for illustration only and are not to be regarded as limiting.

BRIEF DESCRIPTION OF THE DRAWINGS

In the drawings.

FIGS. 1 and 2 are chromatograms of a product of aluminum zirconium glycinate salts made by a known conventional method.

FIGS. 3 and 4 are chromatrograms of the inventive product illustrating the ratio of peak 4 to peak 3 as in the range of 0.5 to 1.8:1.

FIG. 5 and 6 are an aluminum zirconium glycinate salt prepared according to British Patent No. 2,144,992 by heating a 10% solution to 97° C. for 1 hour and 4 hours respectively.

EXAMPLE 1A

PREPARATION OF COMPONENT A 0.576 kg. of an aluminum metal and 3.0 liters of deionized water were charged to a 12 liter reaction flask. 1.02 kg. of 20 degree Baume hydrochloric acid was charged and an exothermic reaction was immediately observed. During the initial reaction stages, an additional 5.15 liters of water was added and the batch temperature was held at 95°–90° C. for 72 hours. A solution of approximately 20% concentration was removed from the excess aluminum, filtered hot and the temperature maintained at 97° C. A sample was analyzed and found to contained 5.26% Al and 3.58% Cl. 0.20 kg. of glycine was dissolved to form a 5/6 basic aluminum chloride-gly complex.

EXAMPLE 1B

PREPARATION OF COMPONENT B 1.95 kg. of a 50% zirconyl hydroxychloride solution with a metal to chloride atomic ratio of 0.96:1 was charged to a 4 liter flask. The contents were heated to 50° C. and 0.20 kg. of glycine was added to form a zirconyl hydroxy chloride-gly complex which is referred to as Component B.

PREPARATION OF ALUMINUM ZIRCONIUM HYDROXY HALIDE - GLYCINATE COMPLEX FROM COMPONENT 1A AND COMPONENT 1B

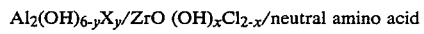

2.65 kg. of Component A at 97° C. was charged to 0.65 kg. of Component B at 50° C. The combined solution was transferred to a spray dryer feed pot where its temperature was maintained at 85° C. The solution was immediately spray dried in a conical bottom lab dryer at 480° F. inlet and 215° F. outlet. The average contact time of the feed solution was approximately 15 minutes.

Three consecutive batches of feed solution were prepared during the drying process to minimize contact time of the components.

Figure 2:
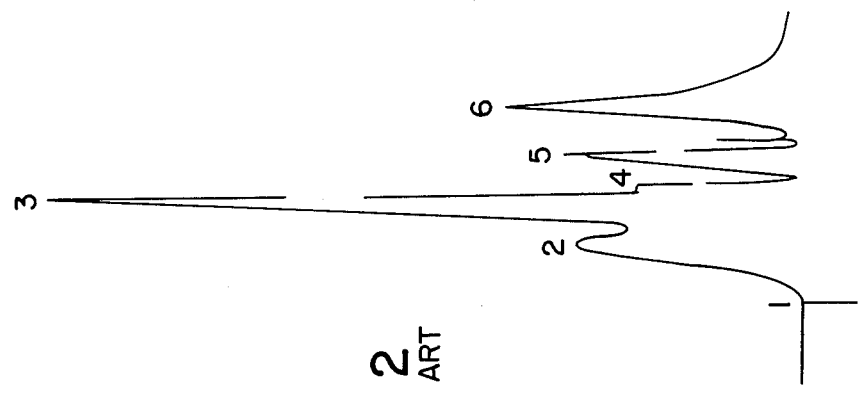
FIGS. 1 to 6 illustrate chromatograms of the product showing the ratio of peak 4 to peak 3.
Figure 1:
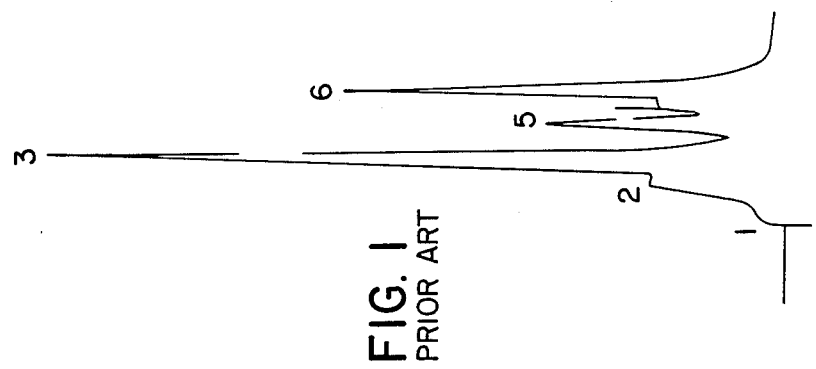
Figure 4:
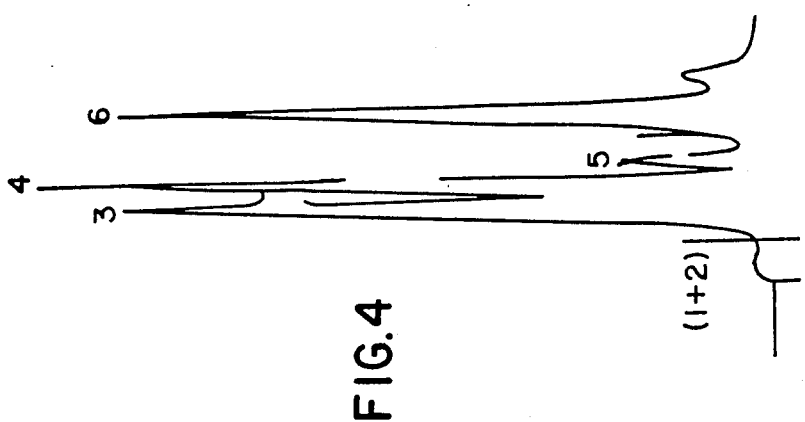
Figure 3:
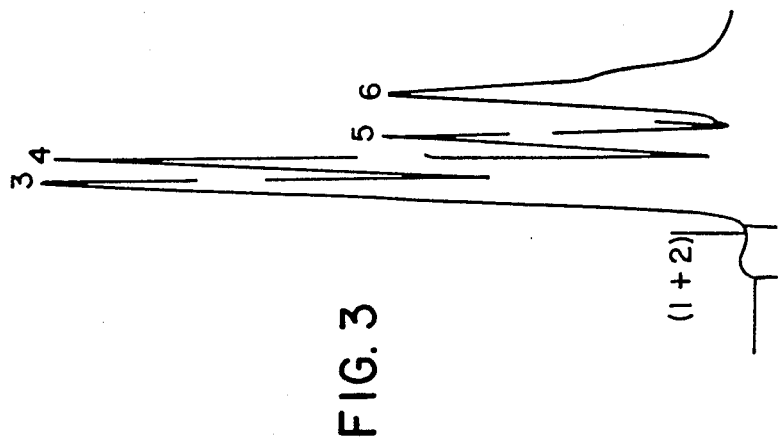

2.57 kg. of an aluminum zirconium hydroxychloride glycinate complex was recovered, analyzed and found to contain 14.9% zirconium and 14.3% aluminum. A sample was subject to gel permeation chromatography and found to contain a peak 4 to peak 3 height ratio of 0.95:1 and 0.7% of polymers in peaks (1 +2) as shown in FIG. 3.

Figure 6:
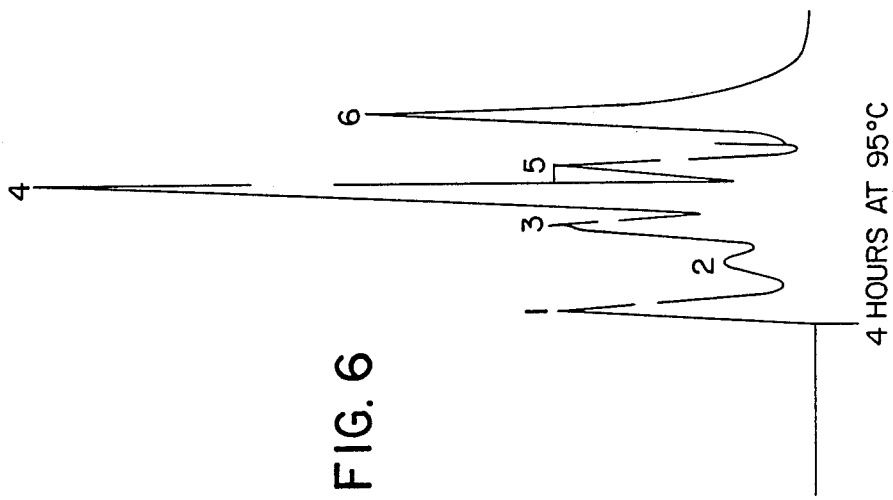
Figure 5:
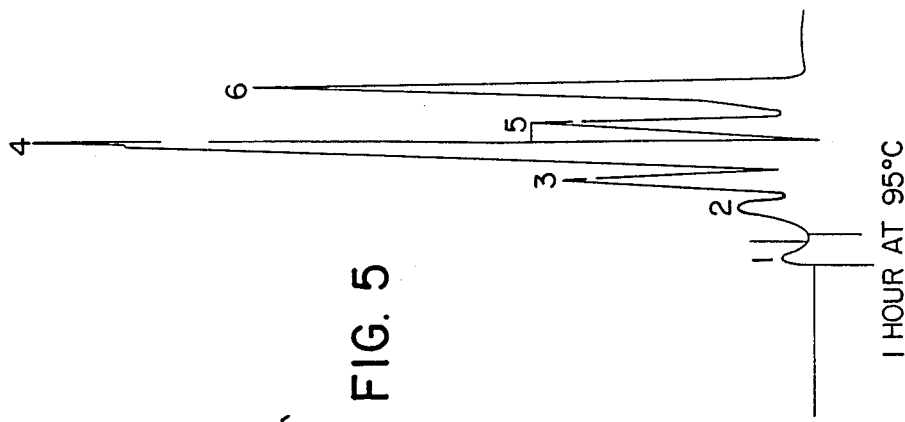

When comparing the chromatograms of the inventive product to the chromatograms of the British product illustrated in FIG. 5 and 6, one readily notes the graphic difference between the ratios of peaks 4 and 3, as well as the presence of more than 4% of the polymer in peaks (1+2) of FIG. 5 and 6. The production of a product with a peak 4 to peak 3 ratio of 0.5 to 1.8:1 and having a narrow polydispersity with little representation of the polymer in either peak 1 or 2 is believed to produce the improved product claimed.

EXAMPLE 2

1.44 kg. aluminum granular ingots were added to a 50 liter round bottom flask with 5.08 kg. deionized water and 2.61 kg. 20 degree Baume hydrochloric acid. An exothermic reaction occurred. During the course of the reaction 12.53 kg. of deionized water was added slowly. The temperature was brought up to 98° C. for 72 hours without refluxing. A condenser was used on the 50 liter flask to maintain a constant volume of water. After 72 hours the aluminum ingots were removed and an analysis was performed. A 20% solution was recovered, analyzed and found to contain 5.01% Aluminum, 3.46% Chloride, Aluminum/Chloride Ratio of 1.90:1. The solution temperature was maintained at 90° C. and labeled Component A.

3.56 kg. of zirconium basic carbonate was added to a 15 liter plastic container with 1.41 kg. 20 degree Baume hydrochloric acid and 10.66 kg. deionized. An exothermic reaction was observed. When the reaction had subsided the solution was placed into a 12 liter round bottom flask and heated to 95° C. with a condenser for two hours without refluxing. 1.20 kg. of glycine was added to form a zirconyl hydroxychloride-glycine solution at 95° C. without refluxing. The analysis showed 6.68% Zirconium, 2.65% Chloride, Zirconium/Chloride ratio of 0.98:1 and 7.06% Glycine. The resulting 20% zirconyl hydroxychloride-gly solution was labeled Component B.

Component B at 95° C. was slowly mixed with stirring with Component A at 90° C. using an addition funnel on a 50 liter round bottom flask with a condenser. The temperature was maintained at 90° C. without refluxing. The HPLC chromatogram taken at a contact time of 15 minutes showed band 4 peak height/band 3 peak height ratio to be 1.41:1, with less than 1% total volume in peaks (1+2). The analysis showed 2.93% Aluminum, 2.71% Zirconium Aluminum/Zirconium ratio of 3.65:1, 3.51% Chloride and 2.87% Glycine.

EXAMPLE 3

1.44 kg. aluminum granular ingots were added to a 50 liter round bottom flask with 4.08 kg. deionized water and 2.61 kg. 20 degree Baume hydrochloric acid. An exothermic reaction occurred. During the course of the reaction 12.53 kg. of deionized water was added slowly. The temperature was brought up to 98° C. for 72 hours without refluxing. A condenser was used on the 50 liter flask to maintain a constant volume of water. After 72 hours the aluminum ingots were removed and an analysis was performed. The result was 5.21% aluminum, 3.57% chloride and an Aluminum/Chloride ratio of 1.92:1. 0.50 kg. of glycine was added to the aluminum chlorhydrate solution with 0.24 kg. of 20 degree Baume hydrochloric acid. The 20% basic aluminum sesquichlorhydrate-gly solution was maintained at 98° C. and labeled Component A.

3.56 kg. of zirconium basic carbonate was added to a 5 liter plastic container with 1.41 kg. 20 degree Baume hydrochloric acid and an exothermic reaction was observed. When the reaction had subsided, the solution was placed into a 12 liter round bottom flask and heated to 95° C. with a condenser for 2 hours with refluxing. 0.50 kg. of glycine was added to the zirconyl hydroxychloride while the solution was still at 95° C. The 50% zirconyl hydroxychloride-gly solution was allowed to cool to 50° C. and was labeled Component B.

Component B at 50° C. was slowly mixed with stirring with Component A at 98° C. using an addition funnel on a 50 liter round bottom flask with a condenser. The resulting temperature for the aluminum zirconium tetrachlorhydrex-gly solution was 84° C. The HPLC chromatogram taken after 15 minutes showed a peak height ratio to be 1.00:1, with less than 1% total volume in peaks (1+2). The analysis showed a 4.46% Aluminum, 3.99% Zirconium, Aluminum/Zirconium ratio 3.78:1, 4.64% Chloride and 3.48 Glycine.

EXAMPLE 4

1.44 kg. aluminum granular ingots were added to a 50 liter round bottom flask with 5.08 kg. deionized water and 2.61 kg. 20 degree Baume hydrochloric acid. An exothermic reaction occurred. During the course of the reaction 12.53 kg. of deionized water was added slowly. The temperature was brought up to 98° C. for 72 hours without refluxing. A condenser was used on the 50 liter flask to maintain a constant volume of water. After 72 hours the aluminum ingots were removed. A 20% aluminum chlorhydrate solution was recovered, analyzed and found to contain 5.18% Aluminum, 3.53% Chloride, Aluminum/Chloride ratio of 1.93:1. 0.64 kg. of glycine was added to the aluminum chlorhydrate solution. The aluminum chlorhydrate-gly solution was labeled Component A.

3.56 kg. of zirconium basic carbonate was added to a 5 liter plastic container with 1.41 kg. 20 degree Baume hydrochloric acid and an exothermic reaction was observed. When the reaction had subsided, the solution was placed into a 12 liter flask and was heated to 95° C. with a condenser for two hours without refluxing. 0.64 kg. of glycine was added while the zirconyl hydroxychloride-gly solution was allowed to cool to 30° C. and was labeled Component B. The analysis showed 19.43% zirconium, 8.04% Chloride, Zirconium/Chloride ratio 0.94:1 and 11.89% Glycine.

Component B at 30° C. was slowly mixed with stirring with Component A at 90° C. using an addition funnel on a 50 liter round bottom flask with a condenser. The resulting temperature for the aluminum zirconium trichlorhydrex-gly was 78° C. The HPLC chromatogram taken at a contact time of 15 minutes showed band 4 peak height/band 3 peak height ratio to be 0.90:1 with less than 1% total volume in peaks (1 & 2). The analysis showed 4.19% Aluminum, 4.09% Zirconium, Aluminum/Zirconium ratio 3.46:1, 4.87% Chloride and 4.85% Glycine.

EXAMPLE 5

2.74 kg. of an aluminum chlorhydrate powder which contained 35.1% of its polymers in Band III was diluted to a 20% concentration with 11.0 kg. of deionized water at 95° C. The temperature was maintained at 95° C. without refluxing 0.43 kg. of glycine was added with stirring. The basic aluminum chlorhydrate-gly was labeled Component A. The analysis was 4.96% Aluminum, 3.26% Chloride, Aluminum/Chloride ratio of 1.98:1 and 2.66% Glycine.

2.04 kg. of zirconium basic carbonate was added to a 5 liter plastic container with 0.80 g. of 20 degree Baume hydrochloric acid. An exothermic reaction was observed. When the reaction had subsided, the solution was placed into a 12 liter flask and was heated to 95° C. with a condenser for 2 hours without refluxing. 0.43 kg. of glycine was added while zirconyl hydroxy chloride solution was still at 95° C. While zirconyl hydroxy chloride-gly solution was allowed to cool to 30° C. and was labeled Component B. The analysis showed 17.78% Zirconium, 7.40% Chloride, 0.93:1 Zirconium/Chloride ratio and 11.11% Glycine.

Component B at 30° C. was slowly mixed with stirring with Component A at 95° C. using an addition funnel on a 12 liter round bottom flask with a condenser. The resulting temperature for the aluminum zirconium trichlorhydrex-gly solution was 77° C. The HPLC chromatrogram taken at a contact time of 15 minutes showed band 4 peak height/band 3 peak height ratio to be 1.06:1 with 0.43% of polymers in peaks (1+2). The analysis showed 4.62% Aluminum, 4.25% Zirconium, Aluminum/Zirconium ratio of 3.68:1, 4.84% Chloride and 5.67% Glycine.

EXAMPLE 6

10 grams of aluminum powder and 20 g. of aluminum granular ingots were reacted with 52 g. HBr (47% Active) and 333 g. deionized water. The reaction temperature was maintained at 95° C. for 24 hours. The solution was filtered and brought back to 95° C., with no refluxing. 3 g. of glycine was added to the aluminum bromohydrate solution and was labeled Component A.

179 g. of zirconium basic carbonate was mixed with 68.0 g. of 20 degree Baume hydrochloric acid in a 4 liter beaker. An exothermic reaction was observed. When the reaction had subsided, the solution was placed into a 500 ml. round bottom flask and was heated to 95° C. with a condenser for 2 hours without refluxing. 15 g. of glycine was added while the zirconyl hydroxy chloride-gly solution was still at 95° C. The zirconyl hydroxy chloride-gly solution was allowed to cool to 30° C. and was labeled Component B.

20 g. of an aluminum chlorhydrate powder, which contained 36.4% of its polymers in Band III, was added to a 500 ml. round bottom flask with 85.7 g. Component A and 14.3 g. Component B. The contact temperature of 85° C. was maintained for 2 hours. The HPLC chromatogram taken at the initial contact of all the components showed the height of peak 4/height of peak 3 ratio to be 0.91:1 with 0.65% of the polymers in peaks (1+2). After 2 hours at the contact temperature of 85° C., the HPLC chromatogram showed the height of peak 4/height of peak 3 ratio to be 0.50:1 with 0.50% of polymers in peaks (1+2).

What is claimed is:

1. An aluminum zirconium hydroxy halide glycinate complex having the empirical formula:

$$Al_2(OH)_{6-y}X_y/ZrO(OH)_xCl_{2-x}/\text{Neutral Amino Acid}$$

wherein x has a numerical value from 0 to 1.5, y has a numerical value from 0.7 to 3.0 and X is chlorine, bromine or iodine and whose polymer distribution as characterized by a size exclusion chromatograph test is:
   (a) a peak height ratio of peak 4 to peak 3 of 0.5 to 1.8:1, and
   (b) peaks (1+2) contain less than 4% of the polymer distribution by weight.

2. The aluminum zirconium hydroxy halide gycinate complex according to claim 1 wherein the quantities of $Al_2(OH)_{6-y}X_y$ and $ZrO(OH)_xCL_{2-x}$ utilized to form the complex are selected so that the ratio of Al to Zr is about 2.0 to about 8.0.

3. The aluminum zirconium hydroxy halide gycinate complex according to claim 1 wherein the quantities of $Al_2(OH)_{6-y}X_y$, $ZrO(OH)_xCl_{2-x}$ and glycinate utilized to form the complex are selected so that the ratio of metal to glycinate is about 1.0 to about 10.0.

4. The complex according to claim 1 wherein the peak height ratio of peak 4 to peak 3 is 0.5 to 1.41:1.

5. The complex according to claim 1 wherein the peak height ratio of peak 4 to peak 3 is 0.5 to 1.00:1.

6. The complex according to claim 1 wherein the peak height ratio of peak 4 to peak 3 is 1.41:1.

7. The complex according to claim 1 wherein the peak height ratio of peak 4 to peak 3 is 1.00:1.

8. A method for preparing an aluminum zirconium hydroxy halide glycinate complex having the empirical formula:

$$Al_2(OH)_{6-y}X_y/ZrO(OH)_xCl_{2-x}/\text{Neutral Amino Acid}$$

wherein x has a numerical value from 0 to 1.5, y has a numerical value from 0.7 to 3.0 and X is chlorine, bromine or iodine which comprises:
   (a) introducing an aqueous solution of Component A comprising 8–35% of a basic aluminum halide at a temperature of 45 to 100° C. and having the empirical formula:

$$Al_2(OH)_{6-y}X_y \cdot nH_2O$$

wherein y has a numerical value from about 0.7 to about 3, X is chlorine, bromine or iodine, and n has a numerical value from about 0.8 to about 4, and whose polymer distribution as characterized by a size exclusion chromatography test has at least 20% of its polymers in Band III and 100% of the aluminum containing polymers in Bands II, III and IV;
   (b) introducing an aqueous solution of Component B comprising a 20–55% solution of zirconyl hydroxychloride having the empirical formula:

$$ZrO(OH)_xCl_{2-x}$$

wherein x is a numerical value of from 0 to 1.5; a neutral amino acid being included in the solutions of either or both of Components A and B;
   (c) mixing component A and Component B at a temperature of from 50° C. to 100° C. for a time period of less than 2 hours to form a combined solution, thereby forming a complex of Component A and Component B; and (d) spray-drying the complex to a powder having a polymer distribution as characterized by the size exclusion chromatography test of:
(1) a peak height ratio of peak 4 to peak 3 of 0.5 to 1.8:1, and
(2) peaks (1+2) of less than 4% of the polymer distribution by weight.

9. The method according to claim 8 wherein said mixing step (c) further comprises:
adding a neutral amino acid to said Component A in an atomic ratio of amino acid to aluminum in a range of 0-3.0:1.

10. The method according to claim 8 wherein said mixing step (c) further comprises:
adding a neutral amino acid to said component B in an atomic ratio of amino acid to zirconium in a range of 0-3.0:1.

11. The method according to claim 8 wherein said amino acid is glycine.

12. The method according to claim 8, wherein said introducing step (a) further comprises using a 20% solution of said Component A.

13. The method according to claim 8, wherein said introducing step (b) further comprises using a 50% solution of said Component B.

14. The method according to claim 2, wherein said temperature of mixing Component A and Component B is about 85° C.

15. The method according to claim 8, wherein said peak height ratio of peak 4 to peak 3 is 1:1.

16. The process according to claim 8 wherein component B comprises about 50 to about 55% zirconyl hydroxychloride.

17. The process according to claim 8 wherein Component A comprises about 17 to 22% by weight of basic aluminum halide.

18. The process according to claim 8 wherein Component A and Component B are mixed for a time of less than 30 minutes.

19. The method according to claim 8 wherein the quantities of $Al_2(OH)_{6-y}X_y$ and $ZrO(OH)_xCl_{2-x}$ utilized to form the complex are selected so that the ratio of Al to Zr is about 2.0 to about 8.0.

20. The method according to claim 8 wherein the quantities of $Al_2(OH)_{6-y}X_y$, $ZrO(OH)_xCl_{2-x}$ and glycinate utilized to form the complex are selected so that the ratio of metal to glycinate is about 1.0 to about 10.0.

21. The process according to claim 8 wherein the peak height ratio of peak 4 to peak 3 is 0.5 to 1.41:1.

22. The process according to claim 8 wherein the peak height ratio of peak 4 to peak 3 is 0.5 to 1.00:1.

23. The process according to claim 8 wherein the peak height ratio of peak 4 to peak 3 is 1. 41:1.

24. The process according to claim 8 wherein the peak height ratio of peak 4 to peak 3 is 1.00:1.

* * * * *